United States Patent [19]
Kenda

[11] Patent Number: 5,807,354
[45] Date of Patent: Sep. 15, 1998

[54] AN IMPLANTABLE CATHETER HAVING INTERMEDIATE LENGTH SECTION OF GREATER FLEXIBILITY THAN REMAINING LENGTHS

[76] Inventor: Rajko Kenda, Staniceva 5b, Ljubljana, Slovenia, 1000

[21] Appl. No.: 750,266

[22] PCT Filed: Jun. 2, 1995

[86] PCT No.: PCT/SI95/00011

§ 371 Date: Dec. 3, 1996

§ 102(e) Date: Dec. 3, 1996

[87] PCT Pub. No.: WO95/33507

PCT Pub. Date: Dec. 14, 1995

[30] Foreign Application Priority Data

Jun. 3, 1994 [SI] Slovenia ............... P-9400248

[51] Int. Cl.$^6$ ............................................. A61M 25/00
[52] U.S. Cl. ................. 604/280; 604/174; 604/282
[58] Field of Search .................... 604/174, 175, 604/264, 280, 281, 282

[56] References Cited

U.S. PATENT DOCUMENTS

| | | | |
|---|---|---|---|
| 3,796,211 | 3/1974 | Kohl | 604/281 |
| 4,516,972 | 5/1985 | Samson | 604/282 |
| 4,564,361 | 1/1986 | Akiyama . | |
| 4,852,564 | 8/1989 | Sheridan et al. | 604/281 |
| 5,125,909 | 6/1992 | Heimberger | 604/264 |
| 5,156,597 | 10/1992 | Verreet et al. | 604/175 |
| 5,314,418 | 5/1994 | Takano et al. | 604/282 |
| 5,363,882 | 11/1994 | Chikama | 604/282 |
| 5,386,826 | 2/1995 | Inglis et al. | 604/282 |
| 5,409,469 | 4/1995 | Schaerf | 604/282 |
| 5,484,424 | 1/1996 | Cottenceau et al. | 604/282 |
| 5,643,226 | 7/1997 | Cosgrove et al. | 604/264 |
| 5,662,616 | 9/1997 | Bousquet | 604/175 |

FOREIGN PATENT DOCUMENTS

| | | |
|---|---|---|
| 588 546 A3 | 3/1994 | European Pat. Off. . |
| 321 666 | 6/1920 | Germany . |

*Primary Examiner*—Mark Bockelman
*Assistant Examiner*—Jennifer R. Sadula
*Attorney, Agent, or Firm*—Jacobson, Price, Holman & Stern, PLLC

[57] ABSTRACT

The invention relates to a catheter, particularly a permanently implanted catheter, particularly a peritoneal-dialysis one, particularly for such peritoneal dialysis where a catheter tube is positioned normally to the surface area at the location of implantation, which catheter consists of a flexible catheter tube and at least one cuff, which is stable in its position on the catheter tube. The catheter tube provides a length segment (A) beginning next to the patient's skin, the general flexibility of the said length segment being greater than that of the remaining length section of the catheter, so that the catheter tube protruding from the patient's abdomen easily bends at the said length segment without collapsing (being squeezed). In a basic embodiment of the invention, the length segment (A) of the catheter consists of a main tube (1) and two mantle tubes (2, 3) fitted individually onto each length section of the said main tube so that a spacing exists between them, whose length corresponds to the said length segment (A), with reinforcing rings (4) being arranged on the main tube (1) in the region of the said length segment (A). The invention foresees several variant embodiments. Further, the invention relates to a novel use of a flexible tube as means for providing a length segment, whose flexibility in comparison to that of the remaining length section(s) of a tube assembly is intentionally accentuated.

12 Claims, 2 Drawing Sheets

AN IMPLANTABLE CATHETER HAVING INTERMEDIATE LENGTH SECTION OF GREATER FLEXIBILITY THAN REMAINING LENGTHS

The invention concerns a permanently implanted peritoneal-dialysis catheter consisting of a flexible catheter tube.

In EP 0 436 154 A1 (Verreet et al.), a *Trascutaner Implantatkatheter* (Ger.), i.e. a transcutaneous implanting catheter is disclosed, which comprises a first section functioning as a manifold conduit, a second section made of a polyurethane fibre fleece, both of them being incorporated subcutaneously, and a third, extracorporal section. The solution of the said reference is intended to strenghten the said third, extracorporal section in comparison to the said second section. Evidently, no constructional measure is foreseen to protect the patients from inflammations caused by irritating the entry/exit site of the catheter, which occurs when dislocating the extracorporal section of the catheter.

The peritoneal dialysis, the approach thereto, the surgical implantation of a peritoneal catheter as well as catheter-related complications such as infections of the catheter exit site and of the subcutaneous tunnel are clearly and systematically analyzed in *Peritoneal Dialysis*, ed. Karl D. Nolph, Kluwer Academic Publishers (1989), Dordrecht, The Netherlands.

Of decisive importance for the beginning of inventive activity was the authors'statement in the above reference that the use of a catheter, which in the case of peritoneal dialysis is practically permanently implanted into the patient, is accompanied i.a. by frequent inflammations of the subcutaneous tunnel, particularly the sinus tract thereof i.e. the section of the subcutaneous tunnel between the catheter entry/exit site and the nearest subcutaneous cuff, and of the entry/exit site itself, by the leaking of the dialysis fluid from the abdominal cavity along the outer mantle surface of the catheter, which particularly occurs with single-cuff catheters, and even by peritonitis.

A basic object of the invention was, therefore, to provide measures for protecting the patients from the said inflammations. One line of investigating the causes of inflammations was based on the supposition that the apparatus involved in the dialysis system was faultless. However, in spite of eliminating the possible subjective causes of infections one after the other, inflammations occurred. It turned out that the infections were mainly caused by the catheter entry/exit site on the patient's abdominal wall being continually irritated due to practically continuous changing of the position of the outer section of the catheter. Due to the movements of the free end of the catheter, the neighbouring patient's tissue is subjected to stretching in all directions with respect to the surface area of the abdomen and, additionally, deformations of the skin in the inward and outward directions as well as spiral windings of the skin and of the subcutaneous layer occur.

It has been established that in spite of using double-cuff catheters (two cuffs mean two retaining/anchoring locations of the catheter in the patient) and in spite of penetrating the patient's skin by the catheter tube normally, or essentially normally, to its surface (normal positioning is less stressful for the skin than angular implantation) and in spite of the catheter tube being made of a biocompatible material, which as such is flexible and (from the point of view of the material) not aggressive to the tissue, which all should have been sufficient for eliminating the foreseeable problems, the catheter in use, when its outer free segment is freely moved, evidently behaves substantially as a rigid body in the region of the sinus section of the tunnel; therefore a local irritation of the mouth of the sinus section cannot be excluded.

A solution of the above problem based on moving one of the cuffs to the surface of the patient's abdominal wall and arranging it there in a suitable manner in order to secure the entry/exit site of the catheter would generate several new problems. Hence the said solution has not been elaborated on.

Finally, the object of the invention crystallized as the question how the catheter tube itself should be constructed in order to provide a sufficient flexibility in the region of the entry/exit site in the abdominal wall to make possible optional movements of the free outer section of the catheter without stressing the tissue and thereby irritating the entry/exit site.

Thus, the object of the invention is to embody a catheter with a special length segment arranged next to the entry/exit site, whose flexibility will be more distinct than that of the proper catheter tube so that in the course of free movements the said length segment will form a continuous bend without running the risk of collapsing (being squeezed).

According to the present invention, a permanently implanted peritoneal-dialysis catheter consisting of a flexible catheter tube is characterized in that protruding from the patient's body said catheter tube provides a minor length segment of a greater general target flexibility in comparison to that of the remaining length section of the catheter, said target flexibility length segment beginning next to the patient's skin, with a retaining element being arranged at a distance from the flexible segment inside the patient's body.

In a first preferred embodiment of the invention, on a main tube two mantle tubes are fitted individually onto each end thereof so that a spacing exists between them, whose length corresponds to said target flexibility length segment, with reinforcing rings being arranged on said main tube in the region of said length segment, the reinforcing rings being held in a stationary manner on said main tube. Said reinforcing rings are round in section, equal to each other and positioned equidistantly.

In a second preferred embodiment of the invention, on a main tube two mantle tubes are fitted individually onto each end thereof so that a spacing exists between them, whose length corresponds to said target flexibility length segment, with a spiral element being arranged on said main tube in the region of said length segment, said spiral element being held in a stationary manner on said main tube.

In a third preferred embodiment of the invention, on a main tube two mantle tubes are fitted individually onto each end thereof so that a spacing exists between them of a length corresponding to said target flexibility length segment, with a spiral element integral with said main tube being arranged thereon in the region of said target flexibility length segment. Preferably, said spiral element is round in section.

In a fourth preferred embodiment of the invention, on a main tube stationary reinforcing rings are provided on its entire length, with the spacing of said reinforcing rings in the region of said target flexibility length segment being greater than that of the reinforcing rings positioned on the remaining length sections of said main tube.

In a fifth preferred embodiment of the invention, on a main tube stationary reinforcing spiral elements are provided on its entire length, with the pitch of thread of said reinforcing spiral element in the region of said target flexibility length segment being greater than that of said spiral elements at the remaining length sections of said main tube, said spiral elements being bound to said main tube.

In a sixth preferred embodiment of the invention, on a main tube stationary reinforcing spiral elements are provided on its entire length, with the pitch of thread of said reinforcing spiral element in the region of said target flexibility length segment being greater than that of said spiral elements at the remaining length sections of said main tube, said spiral elements being integral with said main tube.

In a seventh preferred embodiment of the invention, in the region of said target flexibility length segment said catheter tube provides annular grooves.

In an eighth preferred embodiment of the invention, in the region of said target flexibility length segment said catheter tube provides annular ribs. The outer diameter of the mantle surface of said target flexibility length segment is smaller than that of the remaining length sections of said catheter tube.

Finally, in a ninth preferred embodiment of the invention, in the region of said target flexibility length segment toroidal elements are arranged, which constitute a tubular bellows.

Hereinafter, the invention is disclosed in more detail on the basis of several embodiments shown in the attached drawings. The FIGURES of the drawings are not made to scale and they only have an informative significance.

DESCRIPTION OF THE PREFERRED EMBODIMENTS

Figure 1:
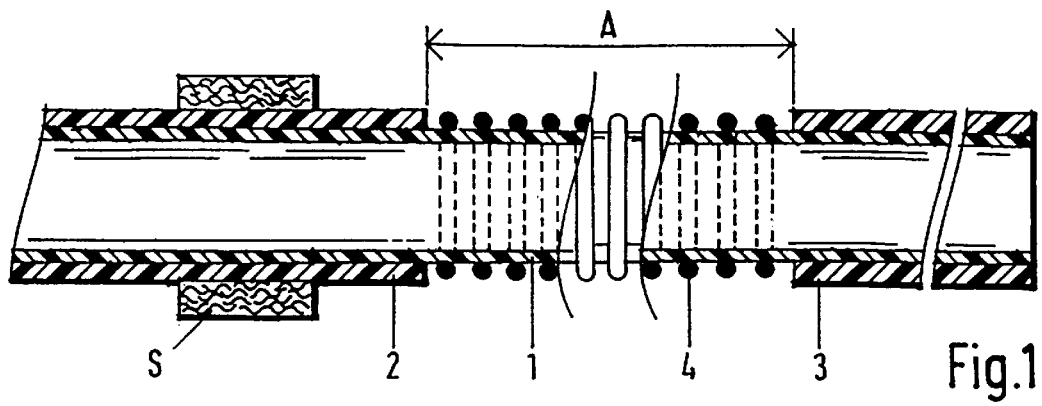
FIG. 1 is a partial cross-sectional view of a proximal region of the catheter of the present invention between a cuff-provided intracorporal region, whose main part is omitted in the drawing, and an extracorporal region, the latter being partly broken.

In each FIGURE a catheter in its sectional view is shown, whose inner section, i.e. the section between a cuff and the inner end of the catheter, is omitted in the drawings since it is taken from the prior art and known to anyone skilled in the art.

According to the invention, the object of the invention is achieved by several approaches.

The catheter of FIG. 1 consists of a main catheter tube 1 suitable for manufacturing catheters (i.e. with a high-degree smoothness of the inner mantle surface), whose one end section is fitted with a mantle tube 2 and its other end section is fitted with a mantle tube 3. An appropriately dimensioned length clearance A is provided between the two mantle tubes 2, 3, where rings 4 are disposed on the mantle surface of the main tube 1. The rings 4 are suitably spaced equidistantly from each other with the two terminal rings 4 being each spaced from the ends of the mantle tubes 2, 3 for a clearance equal to the mutual clearance of rings 4. The rings 4 are preferably circular in section and suitably all uniform and bound to the main tube 1 in an appropriate manner, e.g. glued thereto, so that the stationary state of the rings 4 with respect to the main tube 1 is guaranteed.

The sectional area of the rings 4, their mutual clearance and the spacing of the terminal rings 4 from the ends of the mantle tubes 2, 3 are suitably dimensioned under the consideration of the condition that at an extreme bending of the catheter by the length segment A (meaning the case with the catheter implanted normally to the patient's skin, the curving then amounts to approx. 90°), the rings 4 may at most abut against each other along the line of the inner curve. It follows from the said supposition that also embodiments with rings of different sectional areas are possible within the metes and bounds of the teachings of this invention, e.g. embodiments with the sectional area of the rings increasing or decreasing from the terminal rings towards the middle of the series of rings, or embodiments with a great sectional-area ring followed by a small sectional-area ring and vice versa. It is possible, in the above manner, to influence voluntarily the nature of the curve of the length segment A. With one of the embodiments the said curve is arcuate, with another one it is ellipse-shaped, etc.

As to the above embodiment it is to be noted that it is probably not necessary to extend the main tube 1 of the catheter through the whole length of the mantle tubes 2, 3. If allowed by the manufacturing equipment, the length of the main tube 1 can even be limited to the actual length of the section A with the tube sections 2, 3—now constituting two sections of the proper main tube of the catheter—being directly connected to the former either by abutting or by overlapping.

Figure 2:
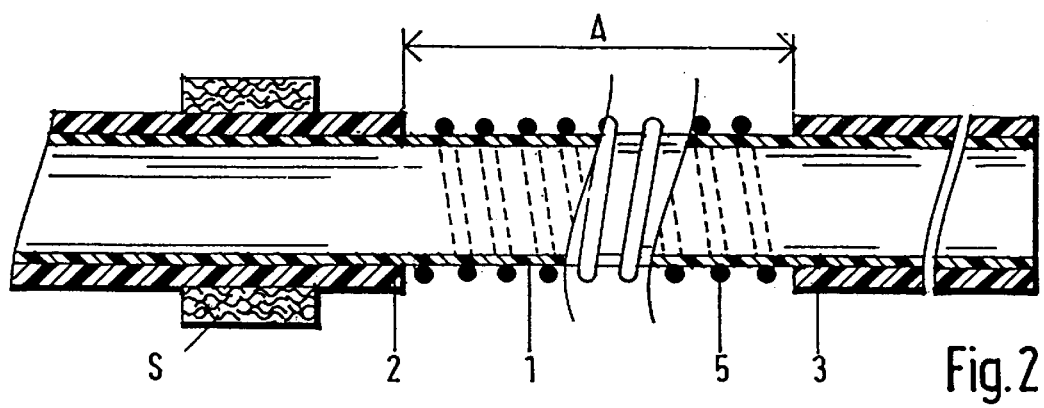
FIG. 2 is a similar partial cross-sectional view of another embodiment of the catheter.

The embodiment shown in FIG. 2 only differs from the above-described one by the use of a spiral element 5 instead of a series of rings 4. Again, the spiral element 5 is made of a circular-section material and fixed as to the position on the tube 1.

Material prototypes of the inventive catheters of FIGS. 1 and 2 as required for carrying out practical tests and for verifying the inventive idea, i.e. for testing the flexibility, used a length segment A between two sections of a prior art catheter tube, which segment was made of a commercially available artificial vein of the type comprising a tube element (similar to the tube 1 in the present case) and a ring-shaped mantle reinforcement (similar to the rings 4) or a spiral-element mantle reinforcement (the spiral element 5), respectively.

Figure 3:
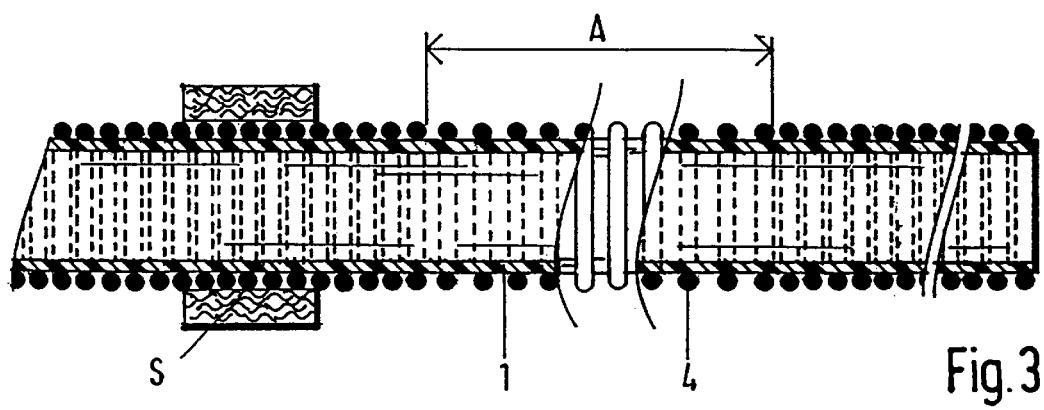
FIG. 3 is a similar partial cross-sectional view of another embodiment of the catheter.
Figure 4:
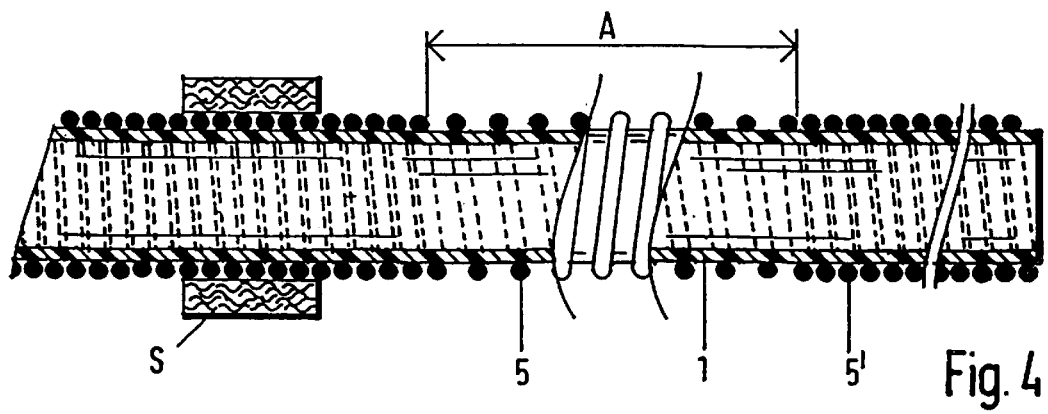
FIG. 4 is a similar partial cross-section view of another embodiment of the catheter.

The embodiments of FIGS. 3 and 4 evidently differ from those of FIGS. 1, 2 in that the mantle tubes 2, 3 of the embodiments of FIGS. 1, 2 are not required. The embodiment of FIG. 3 represents a modification of the embodiment of FIG. 1, the modification being based on the substitution of the mantle tubes 2, 3 by a series of rings 4, mutually uniform, with the density of rings 4 being smaller along the length segment A than along the remaining two length sections of the catheter tube. Analogously, the embodiment of FIG. 4 is a modification of the embodiment of FIG. 2, the modification being based on the substitution of the mantle tubes 2, 3 by spiral elements 5', with the pitch of thread of the spiral element 5 in the length segment A being greater than that of the spiral elements 5'.

The difference of densities of the series of rings 4 in FIG. 3 and of the difference of pitches of threads of the spiral elements. 5, 5' in FIG. 4, respectively, results in that each catheter in the length segment A provides a greater flexibility than in the region of the remaining two length sections.

Figure 5:
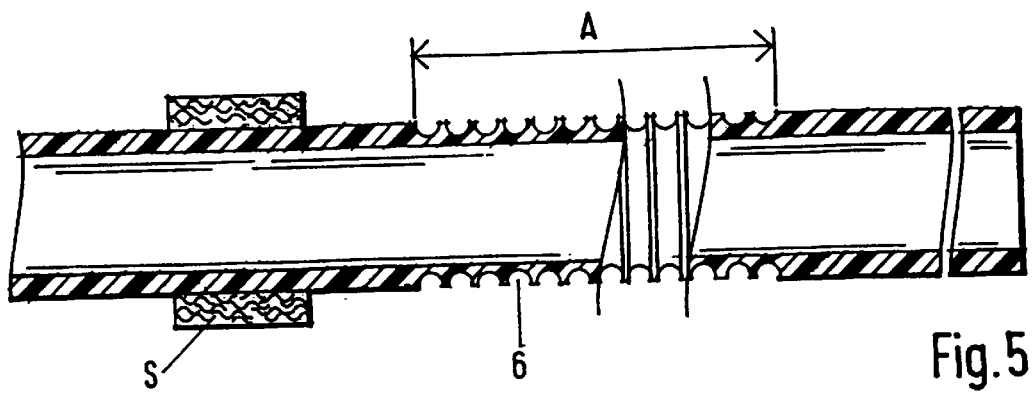
FIG. 5 is a similar partial cross-section view of another embodiment of the catheter.
Figure 6:
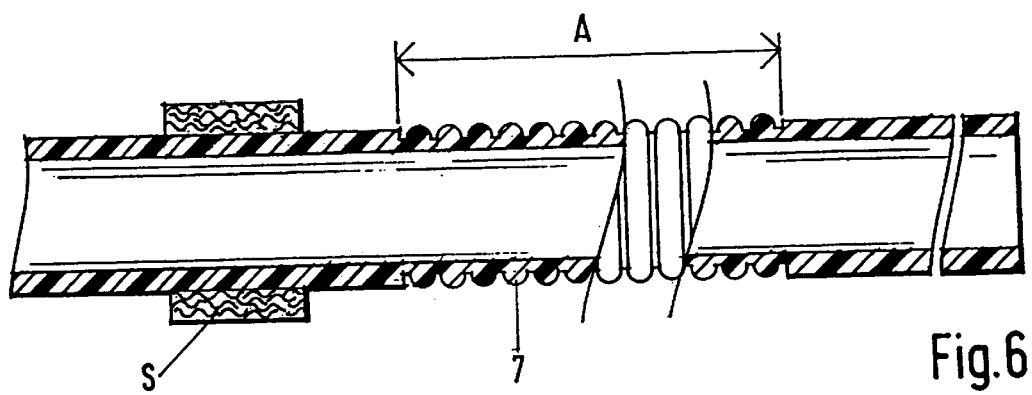
FIG. 6 is a similar partial cross-section view of another embodiment of the catheter.
Figure 7:
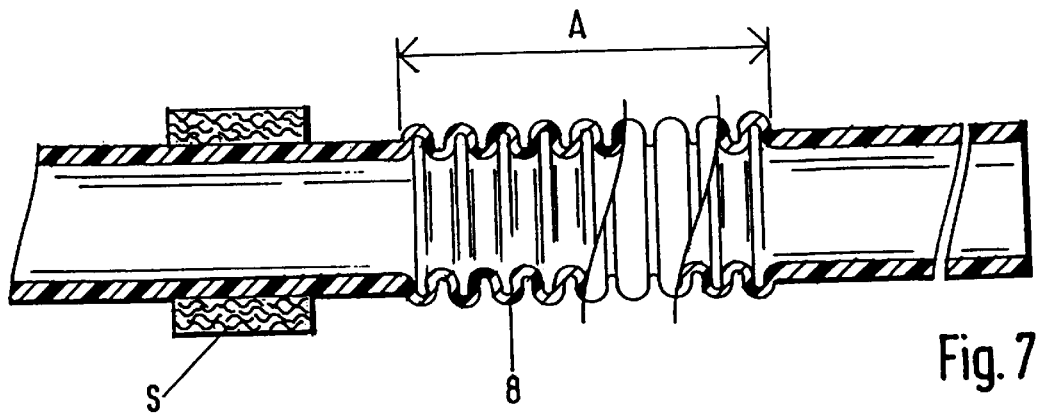
FIG. 7 is a similar partial cross-section view of another embodiment of the catheter.

The following group of inventive solutions shown in FIGS. 5 to 7 are designed by treating the wall construction at the length segment A of a known catheter tube.

In FIG. 5, the wall of the catheter tube is weakened at the length segment A by a series of annular grooves 6. In the embodiment shown, each groove 6 is essentially semicircular in section, the grooves 6 are equal to each other and arranged equidistantly. However, as to the design and size of the section of grooves 6, analogous variations of embodiments as in case of rings 4 disclosed in connection with the embodiment of FIG. I are possible. Although not shown, it is evident that also a possibility of embodying is comprised by the invention, which, instead of grooves 6, foresees a groove spiral, preferably but not exclusively a single-stage one.

FIG. 6 shows a situation that is practically contrary to the one of the preceding embodiment. The outer mantle surface of the catheter at the length segment A, where the diameter of the tube is reasonably reduced in comparison to that of the remaining length sections of the catheter, provides a series of annular ribs 7. In the embodiment shown, each rib 7 is essentially semicircular in section, the ribs 7 being equal to each other and arranged equidistantly. However, as to the design and size of the section of ribs 7, there are again possible analogous variations of embodiments as in case of rings 4 as disclosed in connection with the embodiment of FIG. 1.

Although not shown, it is evident that also a possibility of embodying is comprised by the invention, which, instead of the series of ribs 7, foresees a rib spiral, preferably but not exclusively a single-stage one.

Referring finally to FIG. 7, a further embodiment of a catheter is shown with the tube of the catheter providing increased flexibility at the length segment A, the length segment A being designed as a straight circular-section bellows. In the embodiment shown, the tubular bellows consists of toroidal elements 8, with the elements 8 preferably being equal to each other and arranged so that the nominal diameter of the said elements coincides with that of the catheter tube.

Although not shown, it is again evident that as to the design and size of the section of toroidal elements 8, there are also possible variations as in case of rings 4 of the embodiment of FIG. 1, and that within metes and bounds of the invention an embodiment is also comprised, which, instead of a series of toroidal elements 8, foresees a bulge spiral, provided that the respective manufacturing equipment is available.

Each drawing comprises a schematically shown cuff S, i.e. a retaining element known per se, the cuff being fixed as to the location in the longitudinal direction on the length section of the catheter, which in the implanted state resides inside the patient's body. Practically, the cuff S indicates the respective section of the catheter to be implanted into the patient's body in contrast with the section of the catheter which will protrude from the body. It is thus obvious that the length segment A according to the invention is measured directly from the patient's skin. It is not to be considered impossible to advantageously reduce the spacing between the cuff S and the beginning point of the length segment A when using the catheter according to the invention. The said spacing should be as small as possible and in the prior art catheters it amounts—as stated in the aforementioned literature—to approx. 20 mm (in some cases the said spacing is greater, in others it is smaller). This is a further positive contribution of the disclosed invention to the progress of the respective technical field.

The catheter of the invention can also be used as a permanently implanted hemodialysis catheter. To this end, no retaining element(s) such as retaining element S is required.

I claim:

1. A permanently implanted implantable catherter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said flexible catheter tube includes, a main tube and two mantle tubes fitted onto said main tube so that a spacing exists between each of the two mantle tubes, said spacing defining said minor length section, wherein said main tube between said two mantle tubes includes reinforcing rings about said main tube, the reinforcing rings being held in a stationary manner on said main tube.

2. Catherter of claim 1, wherein each of said reinforcing rings are round in section, of identical configuration, and positioned equidistantly apart from each other.

3. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said flexible catheter tube includes, a main tube and two mantle tubes fitted onto said main tube so that a spacing exists between each of the two mantle tubes, said spacing defining said minor length section, wherein said main tube between said two mantle tubes includes a spiral element held stationary about said main tube.

4. Catheter of claim 3, wherein said spiral element is round in section.

5. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said flexible catheter tube includes, a main tube and two mantle tubes fitted onto said main tube so that a spacing exists between each of the two mantle tubes, said spacing defining said minor length section, wherein said main tube between said two mantle tubes includes a spiral element integral with said main tube.

6. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said catheter tube includes stationary reinforcing rings about its entire length, with the spacing of said reinforcing rings about said minor length section being greater than the spacing of the reinforcing rings positioned on the remaining length sections of said catheter tube.

7. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said catheter tube includes stationary reinforcing spiral elements about its entire length, with the pitch of said reinforcing spiral elements in the region of said minor length section being greater than that of said spiral elements at the remaining length sections, said spiral elements being bound to said catheter tube.

8. Catheter of claim 7 wherein said spiral elements are integral with said catheter tube.

9. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said minor length section of said catheter tube is a tubular bellows having semi-circular bends.

10. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said minor length section of said catheter tube includes annular grooves whose cross-section is semi-circular.

11. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein said minor length section of said catheter tube includes annular ribs whose cross-section is semi-circular.

12. A permanently implantable catheter comprising a flexible catheter tube having an intermediate minor length section of a greater general flexibility in comparison to that of the remaining length sections of the catheter tube, a retaining element on said catheter tube for positioning within the patient's body and arranged at a distance from said minor length section such that said minor length section is adapted to be placed adjacent the patient's skin outside the patient's body, wherein space on said minor length section of said catheter tube has an outer diameter smaller than an outer diameter of the remaining length sections of said catherter tube, and annular ribs protruding radially outward from the outer diameter of said minor length section.

* * * * *